(12) United States Patent
Seely et al.

(10) Patent No.: US 7,576,232 B2
(45) Date of Patent: Aug. 18, 2009

(54) IN SITU MODIFICATION OF MOLYBDENUM-BASED CATALYSTS

(75) Inventors: Michael J. Seely, Naperville, IL (US); Christos Paparizos, Willoughby, OH (US)

(73) Assignee: Ineos USA LLC, Lisle, IL (US)

( * ) Notice: Subject to any disclaimer, the term of this patent is extended or adjusted under 35 U.S.C. 154(b) by 189 days.

(21) Appl. No.: 11/415,565

(22) Filed: May 2, 2006

(65) Prior Publication Data

US 2007/0260085 A1 Nov. 8, 2007

(51) Int. Cl.
*C07C 253/00* (2006.01)
(52) U.S. Cl. .................................... 558/321
(58) Field of Classification Search ........... 558/321, 558/319; 502/304
See application file for complete search history.

(56) References Cited

U.S. PATENT DOCUMENTS 5,175,334 A * 12/1992 Suresh et al. ............... 558/324
6,458,742 B1 * 10/2002 Paparizos et al. ........... 502/304
7,071,140 B2 * 7/2006 Paparizos et al. ........... 502/215
7,348,291 B2 * 3/2008 Paparizos et al. ........... 502/304

* cited by examiner

*Primary Examiner*—Rei-tsang Shiao
(74) *Attorney, Agent, or Firm*—David P. Yusko; James J. Drake; Vik Panchal

(57) ABSTRACT

A process for the conversion of a hydrocarbon selected from the group consisting of propylene, isobutylene, propane, isobutane or mixtures thereof, to acrylonitrile, methacrylonitrile, or mixtures thereof, the process comprising the step of reacting in the vapor phase at an elevated temperature and pressure said hydrocarbon with a molecular oxygen-containing gas and ammonia, in the presence of a molybdenum-based ammoxidation catalyst and a catalyst modifier, wherein said catalyst modifier comprises a molybdate or a polymolybdate of at least one element M selected from the group consisting of cesium, rubidium, potassium, sodium, thallium, lithium, nickel, cobalt, iron, chromium, copper, magnesium, manganese, cerium and phosporus, and wherein the ratio of the M elements to Mo in the molybdate or polymolybdate is greater than the ratio for these M elements to Mo in the molybdenum-based catalyst. The catalyst modifier is useful in modifying the performance of molybdenum-based catalyst and inhibiting molybdenum oxide loss for such catalysts.

13 Claims, No Drawings

IN SITU MODIFICATION OF MOLYBDENUM-BASED CATALYSTS

BACKGROUND OF THE INVENTION

1. Field of the Invention

The present invention relates to an improved process and catalytic mixture for use in the oxidation or ammoxidation of a hydrocarbon to the corresponding product. In one embodiment, the present invention is directed to an improved process for the ammoxidation of propylene, isobutylene, propane, isobutane or mixtures thereof, to acrylonitrile and/or methacrylonitrile. In another embodiment, the present invention is directed to an improved process for the oxidation of propylene, isobutylene, propane, isobutane or mixtures thereof, to acrylic acid and/or methacrylic acid. In these embodiments, the oxidation or ammoxidation occurs in the presence of a molybdenum-based catalyst and a catalyst modifier. More specifically, the modifier can be added to the catalyst in situ, to modify the performance of the catalyst in the reactor and inhibit molybdenum oxide loss from the base catalyst.

2. Description of the Prior Art

Catalysts containing oxides of bismuth and molybdenum, promoted with suitable elements, have long been used for the conversion of propylene at elevated temperatures in the presence of ammonia and oxygen (usually in the form of air) to manufacture acrylonitrile. U.S. Pat. Nos. 5,093,299, 5,212,137, 5,658,842 and 5,834,394 are directed to bismuth-molybdenum promoted catalysts exhibiting high yields to acrylonitrile. Great Britain Patent 1,436,475, U.S. Pat. Nos. 4,766,232, 4,377,534, 4,040,978, 4,168,246, 5,223,469 and 4,863,891 are each directed to bismuth-molybdenum-iron catalysts that may be promoted with the Group II elements to produce acrylonitrile.

Typically, the yield of acrylonitrile is in the upper 70% per pass conversion range, with the remaining products including primarily hydrogen cyanide (HCN), acetonitrile, acrolein, acrylic acid, and carbon oxides. The co-production of HCN and acetonitrile has led to the development of ancillary businesses for these products. The balance of demand for each of these nitriles can dictate the economics for catalyst yields at a given production site. Thus, one production facility may desire to produce more HCN than another.

One approach that has been taken to increase the yield of hydrogen cyanide is to select the operating conditions. However, changing the operating conditions to increase the yield of hydrogen cyanide has always led to an economically unacceptable decrease in the production yields of acrylonitrile.

Specialty catalysts have been developed that increase the yield of hydrogen cyanide co-product produced during the production of acrylonitrile without economically unacceptable losses in acrylonitrile production. For example, U.S. Pat. No. 5,840,648 describes a catalyst that increases the yield of hydrogen cyanide. However it is costly to replace the catalyst charged to a reactor just to modify the yield of certain co-products. A catalyst modifier that can be added in situ and that can increase the yield of desirable co-products, without economically unacceptable losses in acrylonitrile or methacrylonitrile production, is needed.

The decline of catalyst activity after prolonged exposure to ammoxidation conditions, accompanied by a partial loss of molybdenum oxide from the catalyst is often observed. Not only is there a loss of activity, but there is the possibility that the molybdenum oxide lost from the catalyst will deposit onto low temperature surfaces of the reactor system and become scale that is then difficult to remove. U.S. Pat. No. 6,136,998 describes a catalyst that contains small amounts of tellurium, which appears to inhibit the loss of molybdenum oxide from the catalyst. However, a catalyst modifier that can easily be combined with the molybdenum-based catalyst of choice to inhibit molybdenum loss would be desirable.

SUMMARY OF THE INVENTION

The present invention provides a process for the conversion of a hydrocarbon selected from the group consisting of propylene, isobutylene, propane, isobutane or mixtures thereof, to acrylonitrile, methacrylonitrile, or mixtures thereof, the process comprising the step of reacting in the vapor phase at an elevated temperature and pressure said hydrocarbon with a molecular oxygen-containing gas and ammonia, in the presence of a molybdenum-based ammoxidation catalyst and a catalyst modifier, wherein said catalyst modifier comprises a molybdate or polymolybdate of at least one M element selected from the group consisting of cesium, rubidium, potassium, sodium, thallium, lithium, nickel, cobalt, iron, chromium, copper, magnesium, manganese, cerium and phosporus, and wherein the ratio of the M elements to Mo in the molybdates and polymolybdates is greater than the ratio for these M elements to Mo in the molybdenum-based catalyst.

The present invention further provides a catalytic mixture comprising a molybdenum-based catalyst and a catalyst modifier, wherein said catalyst modifier comprises a molybdate or a polymolybdate of at least one M element selected from the group consisting of cesium, rubidium, potassium, sodium, thallium, lithium, nickel, cobalt, iron, chromium, copper, magnesium, manganese, cerium and phosporus, and wherein the ratio of the M elements to Mo in the molybdates and polymolybdates is greater than the ratio for these M elements to Mo in the molybdenum-based catalyst.

The present invention also provides a process for forming a catalytic mixture, the process comprising combining a molybdenum-based ammoxidation catalyst and a solid catalyst modifier comprising a molybdate of or a polymolybdate of at least one of cesium, rubidium, potassium, sodium, thallium, lithium, nickel, cobalt, iron, chromium, copper, magnesium, manganese, cerium and phosporus.

The present invention still further provides a method of inhibiting molybdenum oxide loss from a molybdenum-based catalyst, the method comprising combining a molybdenum-based catalyst and a catalyst modifier, wherein said catalyst modifier comprises a molybdate or a polymolybdate of at least one M element selected from the group consisting of cesium, rubidium, potassium, sodium, thallium, lithium, nickel, cobalt, iron, chromium, copper, magnesium, manganese, cerium and phosporus, and wherein the ratio of the M elements to Mo in the molybdates and polymolybdates is greater than the ratio for these M elements to Mo in the molybdenum-based catalyst.

Further embodiments of the above identified inventions are summarized as follows:

1. The molybdenum-based catalyst and the molybdenum-based ammoxidation catalyst described above may comprise a mixed metal oxide catalyst comprising iron, bismuth and molybdenum.

2. The molybdenum-based catalyst and the molybdenum-based ammoxidation catalyst described above comprise an oxide represented by the following formula:

$$A_a B_b C_c D_d Bi_e Mo_f O_x$$

where
- A is one or more of Li, Na, K, Cs, Rb, Sm, In, Ca, Sr, Ba and Tl,
- B is one or more of Fe, Co, Mg, Mn, Ni, V and Zn,
- C is one or more of Cr, Ce, Eu, P, Sb, Ge, Te and W,
- D is one or more of Sn, B, As, Pt, Pd, Ga, Nd, Nb, Pr and Pb, and
- a is 0.05 to 3.0,
- b is 0.1 to 14.0,
- c is 0.0 to 5.0,
- d is 0.0 to 2.0,
- e is 0.2 to 6.0,
- f is 8.0 to 18.0,
- and x is a number determined by the oxidation states and amounts of the other elements present in the catalyst (i.e. x a number determined by the valence requirements of the other elements present).

3. The molybdenum-based catalyst and the molybdenum-based ammoxidation catalyst described above may comprise an oxide represented by the following formula:

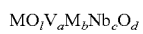

wherein M is one or more of Te and Sb,
- a is 0.01 to 1.0
- b is 0.01 to 1.0
- c is 0.01 to 1.0
- and d is a number determined by the oxidation states and amounts of the other elements present in the catalyst.

4. The catalyst modifier may be impregnated onto a support and calcined.

5. The catalyst modifier may comprise a molybdate or a polymolybdate of at least one element M selected from the group consisting of cesium, rubidium, potassium, sodium, thallium, and lithium.

6 The catalyst modifier may be selected from the group consisting of $Li_2MoO_4$, $Li_2Mo_2O_7$, $Li_6Mo_7O_{24}$, $Li_4Mo_8O_{26}$, $Na_2MoO_4$, $Na_2Mo_2O_7$, $Na_6Mo_7O_{24}$, $Na_4Mo_8O_{26}$, $K_2MoO_4$, $K_2Mo_2O_7$, $K_6Mo_7O_{24}$, $K_4Mo_8O_{26}$, $Rb_2MoO_4$, $Rb_2Mo_2O_7$, $Rb_6Mo_7O_{24}$, $Rb_4Mo_8O_{26}$, $Cs_2MoO_4$, $Cs_2Mo_2O_7$, $Cs_6Mo_7O_{24}$, $Cs_4Mo_8O_{26}$, or mixtures thereof.

7 The catalyst modifier may comprise $Na_2MoO_4$.

8. The catalyst modifier may be added to the molybdenum-based catalyst while the catalyst is operating in the reactor.

9. The catalyst modifier may be coated onto an internal structure of the reactor.

10. The catalyst modifier may coated onto a solid substrate and mounted or placed in a reactor.

11. The molybdenum-based catalyst and said catalyst modifier may be combined to form a catalytic mixture; and this mixture may be added to an oxidation or ammoxidation reactor.

12. In item 11 above, the step of combining the molybdenum-based catalyst and said catalyst modifier may comprise mixing a solid catalyst modifier with fresh molybdenum-based catalyst.

13. In item 11 above, the step of combining the molybdenum-based catalyst and said catalyst modifier may comprise contacting said molybdenum-based catalyst with an aqueous solution or suspension of said catalyst modifier and drying.

DETAILED DESCRIPTION OF THE INVENTION

The instant invention relates to catalyst modifiers and their use with molybdenum-based catalysts. As used herein a "catalyst modifier" is a composition which in the presence of molybdenum-based catalyst during an oxidation or ammoxidation reaction, alters the performance of the molybdenum-based catalyst with respect to the overall performance of the catalyst, the selectivity to products and coproducts produced in the reaction, and/or molybdenum oxide loss from the catalyst during the reaction. As used herein, "molybdenum-based catalyst" refers to a catalyst wherein the molar fraction of molybdenum in the active phase of the catalyst (i.e. excluding supports, diluents, and oxygen) is greater than any other single element of the catalyst. The invention is not limited to modifying any particular molybdenum-based catalyst. Any molybdenum-based catalyst may be modified as described herein.

One embodiment of the instant invention relates to molybdenum-based catalysts that are known in the art for the ammoxidation of propylene to acrylonitrile, such cartalysts are referred to herein as "molybdenum-based ammoxidation catalysts". These catalysts typically comprise a complex of bismuth and molybdenum oxides. The catalysts may further include one or more additional oxides. In one embodiment the molybdenum-based ammoxidation catalyst comprises a mixed metal oxide catalyst comprising iron, bismuth and molybdenum. Such bismuth-molybdenum-iron oxide catalysts promoted with the Group II elements to produce acrylonitrile are described in Great Britain Patent 1,436,475; U.S. Pat. Nos. 4,766,232; 4,377,534; 4,040,978; 4,168,246; 5,223,469 and 4,863,891, each of which is hereby incorporated by reference herein. U.S. Pat. Nos. 5,093,299, 5,212,137, 5,658,842 and 5,834,394 describe bismuth-molybdenum promoted catalysts exhibiting high yields to acrylonitrile, each of which is hereby incorporated by reference herein.

In one or more embodiments, the molybdenum-based catalyst is represented by the following formula:

where
- A is one or more of Li, Na, K, Cs, Rb, Sm, In, Ca, Sr, Ba and Tl,
- B is one or more of Fe, Co, Mg, Mn, Ni, V and Zn,
- C is one or more of Cr, Ce, Eu, P, Sb, Ge, Te and W,
- D is one or more of Sn, B, As, Pt, Pd, Ga, Nd, Nb, Pr and Pb, and
- a is 0.05 to 3.0,
- b is 0.1 to 14.0,
- c is 0.0 to 5.0,
- d is 0.0 to 2.0,
- e is 0.2 to 6.0,
- f is 8.0 to 18.0,
- and x is a number determined by the oxidation states and amounts of the other elements present in the catalyst (i.e. x a number determined by the valence requirements of the other elements present). In certain embodiments, the catalyst comprises oxides of iron, bismuth, and molybdenum, and in one embodiment, comprises a promoted iron-bismuth-molybdenum catalyst.

The catalyst of the present invention may be used either supported or unsupported (i.e. the catalyst may comprise a support). Suitable supports are silica, alumina, zirconium, titania, or mixtures thereof. A support typically serves as a binder for the catalyst resulting in a harder and more attrition resistant catalyst. However, for commercial applications, an appropriate blend of both the active phase (i.e. the complex of catalytic oxides described above) and the support is crucial to obtain an acceptable activity and hardness (attrition resistance) for the catalyst. Directionally, any increase in the active phase decreases the hardness of the catalyst. Typically, the support comprises between 40 and 60 weight percent of the supported catalyst. In one embodiment of this invention, the support may comprise as little as about 30 weight percent of the supported catalyst. In another embodiment of this invention, the support may comprise as much as about 70 weight percent of the supported catalyst. Support materials are available which may contain one or more promoter elements, e.g. a silica sol containing sodium (Na), and such promoter elements may be incorporated into the catalyst via the support material.

In one embodiment the catalyst is supported using a silica sol. If the average colloidal particle diameter of said silica sol is too small, the surface area of the manufactured catalyst will be increased and the catalyst will exhibit reduced selectivity. If the colloidal particle diameter is too large, the manufactured catalyst will have poor anti-abrasion strength. Typically, the average colloidal particle diameter of the silica sol is between about 15 nm and about 50 nm. In one embodiment of this invention, the average colloidal particle diameter of the silica sol is about 10 nm and can be as low as about 8 nm. In another embodiment of this invention, the average colloidal particle diameter of the silica sol is about 100 nm. In another embodiment of this invention, the average colloidal particle diameter of the silica sol is about 20 nm.

The catalysts of the present invention may be prepared by any of the numerous methods of catalyst preparation which are known to those of skill in the art. For example, the catalyst may be manufactured by co-precipitating the various ingredients. The co-precipitating mass may then be dried and ground to an appropriate size. Alternatively, the co-precipitated material may be slurried and spray dried in accordance with conventional techniques. The catalyst may be extruded as pellets or formed into spears in oil as is well known in the art. For particular procedures for manufacturing the catalyst, see U.S. Pat. Nos. 5,093,299; 4,863,891 and 4,766,232, herein incorporated by reference. In one embodiment, the catalyst components may be mixed with a support in the form of the slurry followed by drying or the catalyst components may be impregnated on silica or other supports.

Bismuth may be introduced into the catalyst as an oxide or as a salt which upon calcination will yield the oxide. The water soluble salts which are easily dispersed but form stable oxides upon heat treating are preferred. An especially preferred source for introducing bismuth is bismuth nitrate.

The iron component of the catalyst may be obtained from any compound of iron which, upon calcination will result in the oxides. As with the other elements, water soluble salts are preferred for the ease with which they may be uniformly dispersed within the catalyst. Most preferred is ferric nitrate.

The molybdenum component of the catalyst may be introduced from any molybdenum oxide. However, it is preferred that a hydrolizable or decomposable molybdenum salt be utilized as the source of the molybdenum. The most preferred starting material is ammonium heptamolybdate.

Other required components and optional promoters of the catalyst, (e.g. Ni, Co, Mg, Cr, P, Sn, Te, B, Ge, Zn, In, Ca, W, or mixtures thereof) may be derived from any suitable source. For example, cobalt, nickel and magnesium may be introduced into the catalyst using nitrate salts. Additionally, magnesium may be introduced into the catalyst as an insoluble carbonate or hydroxide which upon heat treating results in an oxide. Phosphorus may be introduced in the catalyst as an alkaline metal salt or alkaline earth metal salt or the ammonium salt but is preferably introduced as phosphoric acid.

Required and optional alkali components of the catalyst (e.g. Rb, Li, Na, K, Cs, Tl, or mixtures thereof) may be introduced into the catalyst as an oxide or as a salt which upon calcination will yield the oxide. Preferably, salts such as nitrates which are readily available and easily soluble are used as the means of incorporating such elements into the catalyst.

The catalysts are typically prepared by mixing an aqueous solution of ammonium heptamolybdate with a silica sol to which a slurry containing the compounds, preferably nitrates of the other elements, is added. The solid material is then dried, denitrified and calcined. Preferably the catalyst is spray-dried at a temperature of between 110° C. to 350° C., preferably 110° C. to 250° C., most preferably 110° C. to 180° C. The denitrification temperature may range from 100° C. to 500° C., preferably 250° C. to 450° C. Finally, calcination takes place at a temperature of between 300° C. to 700° C., preferably between 350° C. to 650° C.

The performance of the molybdenum-based catalyst is modified by the addition of a catalyst modifier. As suggested earlier, such modification includes adjusting selectivity and overall activity of the molybdenum-based catalyst, and inhibiting the loss of molybdenum oxide from the catalyst, while the catalyst is operating in the reactor. For adjusting selectivity and overall activity, the catalyst modifier comprises a molybdate or a polymolybdate of at least one element M selected from the group consisting of cesium, rubidium, potassium, sodium, thallium, and lithium. For inhibiting the loss of molybdenum oxide from the catalyst, the catalyst modifier comprises a molybdate or a polymolybdate of at least one element M selected from the group consisting of cesium, rubidium, potassium, sodium, thallium, lithium, nickel, cobalt, iron, chromium, copper, magnesium, manganese, cerium and phosporus.

The preparation of the molybdates and polymolybdates described herein are known to those skilled in the art. In simplest terms, the molybdates and polymolybdates may be produced by reacting a base (comprising at least one of Cs, Rb, K, Na, Tl, Li, Ni, Co, Fe, Cr, Cu, Mg, Mn, Ce, and P or mixtures thereof) with a molybdenum oxide represented by the formula $Mo_xO_y$, wherein the y/x ratio is in the range of 1 to 3, such molybdenum oxides include (but are not limited to) $MoO_3$, $MoO_2$, $Mo_2O_3$, $Mo_3O_5$, $Mo_4O_{11}$, and $Mo_8O_{23}$. For example, sodium molybdenum dihydrate can be prepared by reacting a slurry of molybdenum oxide ($MoO_3$) with sodium hydroxide, followed by evaporation and crystallization. Additionally, suitable molybdates and polymolybdates are commercially available, for example, sodium molybdate ($Na_2MoO_4$) is available from Climax Molybdenum Company.

Examples of molybdates and polymolybdates are:

| | | | |
|---|---|---|---|
| $Li_2MoO_4$ | $Li_2Mo_2O_7$ | $Li_6Mo_7O_{24}$ | $Li_4Mo_8O_{26}$ |
| $Na_2MoO_4$ | $Na_2Mo_2O_7$ | $Na_6Mo_7O_{24}$ | $Na_4Mo_8O_{26}$ |
| $K_2MoO_4$ | $K_2Mo_2O_7$ | $K_6Mo_7O_{24}$ | $K_4Mo_8O_{26}$ |
| $Rb_2MoO_4$ | $Rb_2Mo_2O_7$ | $Rb_6Mo_7O_{24}$ | $Rb_4Mo_8O_{26}$ |
| $Cs_2MoO_4$ | $Cs_2Mo_2O_7$ | $Cs_6Mo_7O_{24}$ | $Cs_4Mo_8O_{26}$ |

The molybdates and polymolybdates catalyst modifiers described herein are distinguishable over the molybdenum-based catalysts in that the ratio of the M element to Mo (where M is at least one of Cs, Rb, K, Na, Tl, Li, Ni, Co, Fe, Cr, Cu, Mg, Mn, Ce, and P or mixtures thereof) in such molybdates and polymolybdates is significantly greater than the ratio of M to Mo in a molybdenum-based catalyst. Specifically the ratio of M (i.e. all Ms) present in such molybdates and polymolybdates is greater than the ratio of M to Mo in the molybdenum-based catalyst, for those M elements present in both the molybdates or polymolybdates and the molybdenum-based catalyst. In one embodiment, the ratio of M to Mo in the molybdates and polymolybdates is at least 0.5. In another embodiment, the ratio of M to Mo in the molybdates and polymolybdates is at least 0.6. In another embodiment, the ratio of M to Mo in the molybdates and polymolybdates is at least 0.7.

In another embodiment, the present invention provides a process for forming a catalytic mixture, the process including the steps of providing a molybdenum-based oxidation or ammoxidation catalyst, and adding a catalyst modifier comprising a molybdate or a polymolybdate of at least one of cesium, rubidium, potassium, sodium, thallium, lithium, or mixtures thereof. The catalyst modifier may be added to the molybdenum-based catalyst either in situ, i.e. while the catalyst is operating in the reactor, or outside the reactor.

In certain embodiments, the modifier addition does not require liquid phase additions or calcinations. For example, in one embodiment a solid modifier is added to a reactor containing molybdenum-based catalyst. In another embodiment, a solid modifier is mixed with fresh molybdenum-based catalyst, and added to a reactor as make-up catalyst, or when initially charging a reactor. In these or other embodiments, the catalyst modifier is added as a crystalline solid, or as a solid that has been impregnated onto a support and calcined. Suitable supports include those described hereinabove as catalyst supports.

The amount of modifier in the catalytic mixture is not particularly limited. In one embodiment, the amount of modifier is at least about 0.01 weight percent, based upon the total weight of the catalytic mixture, in another embodiment, at least about 0.1, and in yet another embodiment, at least about 0.2 weight percent, based upon the total weight of the catalytic mixture. In these or other embodiments, the amount of modifier is from about 0.01 to about 5 weight percent, or from about 0.1 to about 2 weight percent, or from about 0.2 to about 0.6 weight percent, based upon the total weight of the catalytic mixture. If desired, the catalyst modifier can be added in increments.

In embodiments where the catalyst modifier is supported, the combined amount of modifier plus support can be up to about 30 weight percent, based upon the total weight of the catalyst and catalyst modifier, and is typically less than about 20 weight percent, based upon the total weight of the catalyst and catalyst modifier.

In still other embodiments, the catalyst modifier may be coated onto an internal structure of the reactor (e.g. sidewalls, diplegs, baffles), or onto a solid substrate (e.g. an inert ceramic surface) and then mounted or placed in the reactor.

In one embodiment, the catalyst modifiers of the instant invention are useful in ammoxidation processes. More specifically, the catalyst modifiers of the present invention are useful in a process for the conversion of an olefin selected from the group consisting of propylene, isobutylene, or mixtures thereof, to acrylonitrile, methacrylonitrile, respectively, or mixtures thereof, the process comprising the step of reacting in the vapor phase at an elevated temperature and pressure said olefin with a molecular oxygen-containing gas and ammonia, in the presence of a molybdenum-based ammoxidation catalyst and a catalyst modifier.

Preferably, the olefin ammoxidation reaction is performed in a fluid bed reactor although other types of reactors such as transport line reactors are envisioned. Fluid bed reactors for the manufacture of acrylonitrile are well known in the prior art. For example, the reactor design set forth in U.S. Pat. No. 3,230,246, herein incorporated by reference, is suitable.

Conditions for the ammoxidation reaction of propylene to acrylonitrile to occur are also well known in the prior art as evidenced by U.S. Pat. Nos. 5,093,299; 4,863,891; 4,767,878 and 4,503,001; herein incorporated by reference. Typically, the ammoxidation process is performed by contacting propylene or isobutylene in the presence of ammonia and oxygen with a fluid bed catalyst at an elevated temperature to produce the acrylonitrile or methacrylonitrile. Any source of oxygen may be employed. For economic reasons, however, it is preferred to use air. The reaction is carried out at a temperature of between the ranges of about 260° C. to 600° C. The contact time, although not critical, is generally in the range of 0.1 to 50 seconds, with preference being to a contact time of 1 to 15 seconds. The products of reaction may be recovered and purified by any of the methods known to those skilled in the art. One such method involves scrubbing the effluent gases from the reactor with cold water or an appropriate solvent to remove the products of the reaction and then purifying the reaction product by distillation.

The catalyst modifiers of the present invention are also useful to modify the molybdenum-based catalysts employed in the ammoxidation of propane to acrylonitrile. Conditions for the ammoxidation reaction of propane to acrylonitrile to occur are also well known in the prior art as evidenced by U.S. Pat. No. 5,175,334; herein incorporated by reference. Typically, the ammoxidation process is performed by contacting propane or isobutane in the presence of ammonia and oxygen with a fluid bed catalyst at an elevated temperature to produce the acrylonitrile or methacrylonitrile. Any source of oxygen may be employed. For economic reasons, however, it is preferred to use air. The reaction is carried out at a temperature of between the ranges of about 260° C. to 600° C. The contact time, although not critical, is generally in the range of 0.1 to 50 seconds, with preference being to a contact time of 1 to 15 seconds. The products of reaction may be recovered and purified by any of the methods known to those skilled in the art. One such method involves scrubbing the effluent gases from the reactor with cold water or an appropriate solvent to remove the products of the reaction and then purifying the reaction product by distillation.

In certain embodiments, the yield of hydrogen cyanide is increased when a catalyst modifier is employed according to the present invention. In these or other embodiments, the amount of molybdenum oxide lost from the molybdenum-based catalyst is reduced, when compared to the molybdenum oxide lost when no modifier is present. By reducing the loss of molybdenum oxide, it is possible to reduce the amount of molybdenum oxide scale that builds up on reactor cooling cools or other surfaces.

While the invention thus far has been described largely in reference to processes for the ammoxidation of propylene to acrylonitrile. Another embodiment of the instant invention is the use of the modifiers as previously described herein with molybdenum-based ammoxidation catalysts that are known in the art for the ammoxidation of propane to acrylonitrile. In one embodiment, such catalysts comprise oxides of molybdenum, vanadium, niobium and at least one of tellurium and antimony. Such catalysts may additionally include one or more additional elements. In one or more embodiments, the molybdenum-based catalyst comprise an oxide represented by the following formula:

$$Mo_1V_aM_bNb_cO_d$$

Wherein M is one or more of Te and Sb, a is 0.01 to 1.0 b is 0.01 to 1.0 c is 0.01 to 1.0 and d is a number determined by the oxidation states and amounts of the other elements present in the catalyst (i.e. f a number determined by the valence requirements of the other elements present).

The molybdenum-based catalyst represented by the above formula may additionally comprise one or more promoters and/or additional elements and metal oxides. Representative molybdenum-based propane ammoxidation catalysts and their operating parameters for the ammoxidation of propane to acrylonitrile are described in U.S. Pat. Nos. 5,750,760, 6,036,880 and 6,653,253, each of which is hereby incorporated by reference herein.

Still another embodiment of the instant invention is the use of the modifiers as previously described herein with molybdenum-based oxidation catalysts that are known in the art for use in various oxidation processes, for example, the oxidation of propylene, isopropylene, propane and/or isopropane to acrolein, methacrolein, acrylic acid and/or methacylic acid.

SPECIFIC EMBODIMENTS

In order to illustrate the instant invention, samples of a base catalyst, with and without various catalyst modifiers, were prepared and then evaluated under similar reaction conditions. In each case, the molybdenum-based catalyst was a promoted iron-bismuth-molybdenum catalyst of the type described in U.S. Pat. No. 5,093,299. The active phase of these catalysts contained no Na, Li or Rb, consequently the ratio of the M element(s) to Mo for the molybdenum based catalyst was zero. These examples are provided for illustrative purposes only.

All testing was conducted in a 40 cc fluid bed reactor. Propylene was feed into the reactor at a rate of 0.06 WWH (i.e. weight of propylene/weight of catalyst/hour). Pressure inside the reactor was maintained at 10 psig. Reaction temperature was 430° C. Samples of reaction products were collected after 20 hours, unless otherwise indicated. Reactor effluent was collected in bubble-type scrubbers containing cold HCl solution. Off-gas rate was measured with soap film meter, and the off-gas composition was determined at the end of the run with the aid of gas chromatograph fitted with a split column gas analyzer. At the end of the recovery run, the entire scrubber liquid was diluted to approximately 200 gms with distilled water. A weighted amount of 2-butanone was used as internal standard in a 50 grams aliquot of the dilute solution. A 2 μl sample was analyzed in a GC fitted with a flame ionization detector and a Carbowax column. The amount of $NH_3$ was determined by titrating the free HCl excess with NaOH solution. The following examples are illustrative of our invention.

In Tables 1-6, $C_3$= is propylene, AN is acrylonitrile, and Aceto is acetonitrile. Example C1 is an equilibrated base catalyst. In Examples 2-3, a catalyst modifier was added to the base catalyst of Example C1 as a dry powder, in an amount of 0.5 percent by weight, based on the total weight of the catalyst and modifier.

TABLE 1

| Ex. # | Catalyst Modifier | % Conver | % AN | % HCN | % Aceto | % Acrolein | % Acrylic Acid |
|---|---|---|---|---|---|---|---|
| C1 | None | 97.4 | 79.0 | 5.6 | 1.9 | 0.7 | 1.7 |
| 2 | $Rb_2MoO_4$ | 98.7 | 78.3 | 7.2 | 1.5 | 0.3 | 1.0 |
| 3 | $Cs_2MoO_4$ | 96.6 | 77.6 | 6.7 | 1.4 | 0.2 | 1.1 |

The rubidium and cesium modifiers resulted in increased yields of HCN and lower yields of acrylonitrile.

Example C4 is an equilibrated base catalyst. Examples 5-9 were taken after various hours on stream after the catalyst modifier was added to the molybdenum-based catalyst of Example C4.

TABLE 2

| Ex. # | Catalyst Modifier | % Conv | % AN | % HCN | % Aceto | % Acrolein | % Acrylic Acid |
|---|---|---|---|---|---|---|---|
| C4 | None | 98.7 | 80.7 | 4.2 | 2.1 | 0.2 | 1.9 |
| 5 | $Na_2MoO_4$ 2.4 hours | 98.7 | 79.9 | 5.5 | 2.4 | 0.1 | 1.2 |
| 6 | $Na_2MoO_4$ 5.5 hours | 98.6 | 80.1 | 5.7 | 2.1 | 0.04 | 0.8 |
| 7 | $Na_2MoO_4$ 21.8 hours | 98.5 | 79.5 | 6.1 | 2.4 | 0.06 | 0.9 |
| 8 | $Na_2MoO_4$ 118.5 hours | 97.9 | 79.9 | 6.0 | 2.4 | 0.07 | 0.7 |
| 9 | $Na_2MoO_4$ 363 hours | 97.1 | 79.6 | 6.2 | 2.3 | 0.08 | 0.7 |

As shown in Table 2, the addition of $Na_2MoO_4$ provided a rapid increase in HCN yield, and the HCN yield remained high after 363 hours onstream.

Example C10 is an equilibrated base catalyst. In Examples 11-12, 0.33 percent by weight catalyst modifier, based upon the total weight of the molybdenum-based catalyst and modifier, was added to the base catalyst of Example C10.

TABLE 3

| Ex. # | Catalyst Modifier | % Conv | % AN | % HCN | % Aceto | % Acrolein | % Acrylic Acid |
|---|---|---|---|---|---|---|---|
| C10 | None | 98.7 | 82.2 | 5.1 | 2.3 | 0.3 | 1.7 |
| 11 | $Na_2MoO_4$ | 97.9 | 81.2 | 5.7 | 2.3 | 0.1 | 0.8 |
| 12 | $Li_2MoO_4$ | 98.7 | 80.0 | 6.2 | 2.3 | 0.2 | 1.1 |

As shown in Table 3, the yield of HCN increased, and the yield of acrylonitrile decreased.

Example C13 is an equilibrated molybdenum-based catalyst. Example 14 contains the molybdenum-based catalyst of Example C13, and 0.33 percent by weight catalyst modifier, based on the total weight of catalyst and modifier.

TABLE 4

| Ex. # | Catalyst Modifier | % Conv. | % AN | % HCN | % Aceto | % Acrolein | % Acrylic Acid |
|---|---|---|---|---|---|---|---|
| C13 | None | 98.6 | 80.5 | 5.2 | 2.1 | 0.3 | 1.4 |
| 14 | $K_2MoO_4$ | 97.5 | 77.9 | 6.5 | 1.9 | 0.3 | 1.0 |

As shown in Table 4, the yield of HCN increased, and the yield of acrylonitrile decreased.

The presence of the catalyst modifier also reduces the molybdenum loss experience by molybdenum-based catalysts while in use. In Examples C15-C17 and 18-21, fresh, i.e. unequilibrated catalyst or catalytic mixture was charged to a reactor, and the amount of molybdenum oxide lost from the catalyst was measured after about 24 hours on-stream. Examples C15-C17 were molybdenum-based catalyst, and Examples 18-21 were molybdenum-based catalyst plus 0.33 weight percent sodium molybdate. Molybdenum oxide loss was determined by collecting and weighing molybdenum oxide scale that had accumulated in the test reactor.

TABLE 5

| Ex. # | MoO$_3$ Loss (g) |
|---|---|
| C15 | 1.003 |
| C16 | 1.250 |
| C17 | 1.325 |
| Average | 1.193 |
| 18 | 0.975 |
| 19 | 0.426 |
| 20 | 0.864 |
| 21 | 0.776 |
| Average | 0.685 |

As shown in Table 5, molybdenum oxide loss was reduced by about 57 percent in the samples having a catalyst modifier present.

Lastly, while it has been shown in the above examples that the addition of the molybdate modifier will result in increased yields of HCN and lower yields of acrylonitrile, this effect is reversible by the addition of a molybdenum oxide (e.g. MoO3, ammonium heptamolybdate). This is shown in Table 6 below. In Table 6, Example C22 is the equilibrated molybdenum-based catalyst. Example 23 contains the molybdenum-based catalyst of Example C22, and 0.33 percent by weight catalyst modifier, based on the total weight of catalyst and modifier. Example 24 contains the molybdenum-based catalyst and catalyst modifier of Example 23, and 0.33 percent by weight MoO$_3$, based on the total weight of catalyst, modifier MoO$_3$.

TABLE 6

| Ex. # | Catalyst Modifier | % Conv. | % AN | % HCN | % Aceto | % Acrolein | % Acrylic Acid |
|---|---|---|---|---|---|---|---|
| C22 | Base | 98.6 | 83.2 | 5.1 | 1.7 | 0.2 | 1.2 |
| 23 | Na$_2$MoO$_4$ | 99.4 | 82.1 | 5.9 | 1.6 | 0.1 | 1.4 |
| 24 | MoO$_3$ | 99.3 | 82.8 | 5.6 | 1.6 | 0.1 | 1.5 |

While the foregoing description and the above embodiments are typical for the practice of the instant invention, it is evident that many alternatives, modifications, and variations will be apparent to those skilled in the art in light of this description. Accordingly, it is intended that all such alternatives, modifications and variations are embraced by and fall within the spirit and broad scope of the appended claims.

We claim:

1. A process for the conversion of a hydrocarbon selected from the group consisting of propylene, isobutylene, propane, isobutane or mixtures thereof, to acrylonitrile, methacrylonitrile, or mixtures thereof, the process comprising contacting in a reactor and reacting in the vapor phase at an elevated temperature and pressure said hydrocarbon with a molecular oxygen-containing gas and ammonia, in the presence of a molybdenum-based ammoxidation catalyst and a catalyst modifier, wherein said molybdenum-based ammoxidation catalyst comprises an oxide represented by the following formula:

$A_a B_b C_c D_d Bi_e Mo_f O_x$ where
A is one or more of Li, Na, K, Cs, Rb, Sm, In, Ca, Sr, Ba and Tl,
B is one or more of Fe, Co, Mg, Mn, Ni, V and Zn,
C is one or more of Cr, Ce, Eu, P, Sb, Ge, Te and W,
D is one or more of Sn, B, As, Pt, Pd, Ga, Nd, Nb, Pr and Pb, and
a is 0.05 to 3.0,
b is 0.1 to 14.0,
c is 0.0 to 5.0,
d is 0.0 to 2.0,
e is 0.2 to 6.0,
f is 8.0 to 18.0,
and x is a number determined by the oxidation states and amounts of the other elements present in the catalyst (i.e. x a number determined by the valence requirements of the other elements present); and
wherein said catalyst modifier comprises a molybdate or a polymolybdate of at least one element M selected from the group consisting of cesium, rubidium, potassium, sodium, thallium, lithium, nickel, cobalt, iron, chromium, copper, magnesium, manganese, cerium and phosphorus.

2. The process of claim 1, wherein the catalyst modifier is impregnated onto a support and calcined.

3. The process of claim 1, wherein catalyst modifier comprises a molybdate or a polymolybdate of at least one element M selected from the group consisting of cesium, rubidium, potassium, sodium, thallium, and lithium.

4. The process of claim 1, wherein the catalyst modifier is selected from the group consisting of Li$_2$MoO$_4$, Li$_2$Mo$_2$O$_7$, Li$_6$Mo$_7$O$_{24}$, Li$_4$Mo$_8$O$_{26}$, Na$_2$MoO$_4$, Na$_2$Mo$_2$O$_7$, Na$_6$Mo$_7$O$_{24}$, Na$_4$Mo$_8$O$_{26}$, K$_2$MoO$_4$, K$_2$Mo$_2$O$_7$, K$_6$Mo$_7$O$_{24}$, K$_4$Mo$_8$O$_{26}$, Rb$_2$MoO$_4$, Rb$_2$Mo$_2$O$_7$, Rb$_6$Mo$_7$O$_{24}$, Rb$_4$Mo$_8$O$_{26}$, Cs$_2$MoO$_4$, Cs$_2$Mo$_2$O$_7$, Cs$_6$Mo$_7$O$_{24}$, Cs$_4$Mo$_8$O$_{26}$, or mixtures thereof.

5. The process of claim 1, wherein the catalyst modifier comprises Na$_2$MoO$_4$.

6. The process of claim 1, wherein catalyst modifier is added to the molybdenum-based catalyst while the catalyst is operating in the reactor.

7. The process of claim 1, wherein the catalyst modifier is coated onto an internal structure of the reactor.

8. The process of claim 1, wherein the catalyst modifier is coated onto a solid substrate and mounted or placed in a reactor.

9. The process of claim 1, wherein the process further comprises the steps of:
combining said molybdenum-based ammoxidation catalyst and said catalyst modifier to form a catalytic mixture; and
adding said catalytic mixture to an ammoxidation reactor.

10. The process of claim 9, wherein said step of combining comprises mixing a solid catalyst modifier with fresh molybdenum-based catalyst.

11. The process of claim 9, wherein said step of combining comprises contacting said molybdenum-based catalyst with an aqueous solution or suspension of said catalyst modifier and drying.

12. The process of claim 1, wherein the ratio of the M elements to Mo in the molybdates and polymolybdates is greater than the ratio for these M elements to Mo in the molybdenum-based ammoxidation catalyst.

13. The process of claim 1, wherein the molybdates and polymolybdates are produced by reacting a base, comprising at least one of cesium, rubidium, potassium, sodium, thallium, lithium, nickel, cobalt, iron, chromium, copper, magnesium, manganese, cerium and phosphorus or mixtures thereof, with a molybdenum oxide represented by the formula Mo$_x$O$_y$, wherein the y/x ratio is in the range of 1 to 3.

* * * * *